(12) United States Patent
Rezach

(10) Patent No.: US 11,832,851 B1
(45) Date of Patent: Dec. 5, 2023

(54) SPINAL IMPLANT SYSTEM AND METHODS OF USE

(71) Applicant: Warsaw Orthopedic, Inc., Warsaw, IN (US)

(72) Inventor: William Alan Rezach, Covington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 17/744,920

(22) Filed: May 16, 2022

(51) Int. Cl.
*A61B 17/70* (2006.01)
*A61B 17/86* (2006.01)

(52) U.S. Cl.
CPC ...... *A61B 17/7032* (2013.01); *A61B 17/7037* (2013.01); *A61B 17/7038* (2013.01); *A61B 17/8605* (2013.01)

(58) Field of Classification Search
CPC .. A61B 17/7032; A61B 17/7034–7035; A61B 17/7037–7038; A61B 17/7041
See application file for complete search history.

(56) References Cited

U.S. PATENT DOCUMENTS

| | | | |
|---|---|---|---|
| 6,736,820 B2 | 5/2004 | Biedermann et al. | |
| 6,974,460 B2 | 12/2005 | Carbone et al. | |
| 8,506,600 B2 | 8/2013 | Carbone et al. | |
| 8,864,803 B2 | 10/2014 | Biedermann et al. | |
| 10,603,083 B1* | 3/2020 | Gladieux | A61B 17/7002 |
| 2003/0055426 A1* | 3/2003 | Carbone | A61B 17/7037 606/305 |
| 2005/0154393 A1* | 7/2005 | Doherty | A61B 17/7037 606/267 |
| 2007/0123870 A1* | 5/2007 | Jeon | A61B 17/7037 606/328 |
| 2012/0041495 A9 | 2/2012 | Biedermann et al. | |
| 2012/0303063 A1* | 11/2012 | Cahill | A61B 17/7023 606/267 |
| 2013/0096618 A1* | 4/2013 | Chandanson | A61B 17/888 606/278 |
| 2016/0220281 A1* | 8/2016 | Biedermann | A61B 17/7038 |

FOREIGN PATENT DOCUMENTS

CN 112932640 A * 6/2021 ......... A61B 17/7032

* cited by examiner

*Primary Examiner* — Eduardo C Robert
*Assistant Examiner* — Michelle C Eckman
(74) *Attorney, Agent, or Firm* — Sorell, Lenna & Schmidt, LLP

(57) ABSTRACT

A spinal construct includes a first member. The first member includes a proximal portion defining a first cavity and a distal portion defining a second cavity disposed at an angle relative to the first cavity. The distal portion is configured for connecting with a second member. The second member is configured for fixation with vertebral tissue. A crown defines a first opening aligned with the first cavity and a second opening aligned with the second cavity. Implants, systems, instruments and methods are disclosed.

18 Claims, 10 Drawing Sheets

SPINAL IMPLANT SYSTEM AND METHODS OF USE

TECHNICAL FIELD

The present disclosure generally relates to medical devices for the treatment of spinal disorders, and more particularly to a surgical implant system including one or more bone fasteners and related methods of use.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a spinal construct is provided. The spinal construct includes a first member. The first member includes a proximal portion defining a first cavity and a distal portion defining a second cavity disposed at an angle relative to the first cavity. The distal portion is configured for connecting with a second member. The second member is configured for fixation with vertebral tissue. A crown defines a first opening aligned with the first cavity and a second opening aligned with the second cavity. In some embodiments, implants, systems, instruments and methods are disclosed.

In one embodiment, a bone fastener is provided. The bone fastener includes a receiver. The receiver includes a proximal portion defining a first cavity and a distal portion defining a second cavity disposed at an angle relative to the first cavity. A shaft is connected with the distal portion and configured for fixation with vertebral tissue. A crown defines a first opening aligned with the first cavity and a second opening aligned with the second cavity. The crown is releasably engageable with an inner surface of the distal portion such that the crown is movable between a provisional orientation with the receiver and a fixed orientation with the receiver and the shaft.

In one embodiment, a spinal implant system is provided. The spinal implant system includes a first member including a proximal portion defining a first cavity and a distal portion defining a second cavity disposed at an angle relative to the first cavity. A second member is connectable with the distal portion and is configured for fixation with vertebral tissue. A crown defines a first opening aligned with the first cavity and a second opening aligned with the second cavity. A longitudinal element is disposable in the first cavity.

BRIEF DESCRIPTION OF THE DRAWINGS

The present disclosure will become more readily apparent from the specific description accompanied by the following drawings, in which.

DETAILED DESCRIPTION

Figure 1:
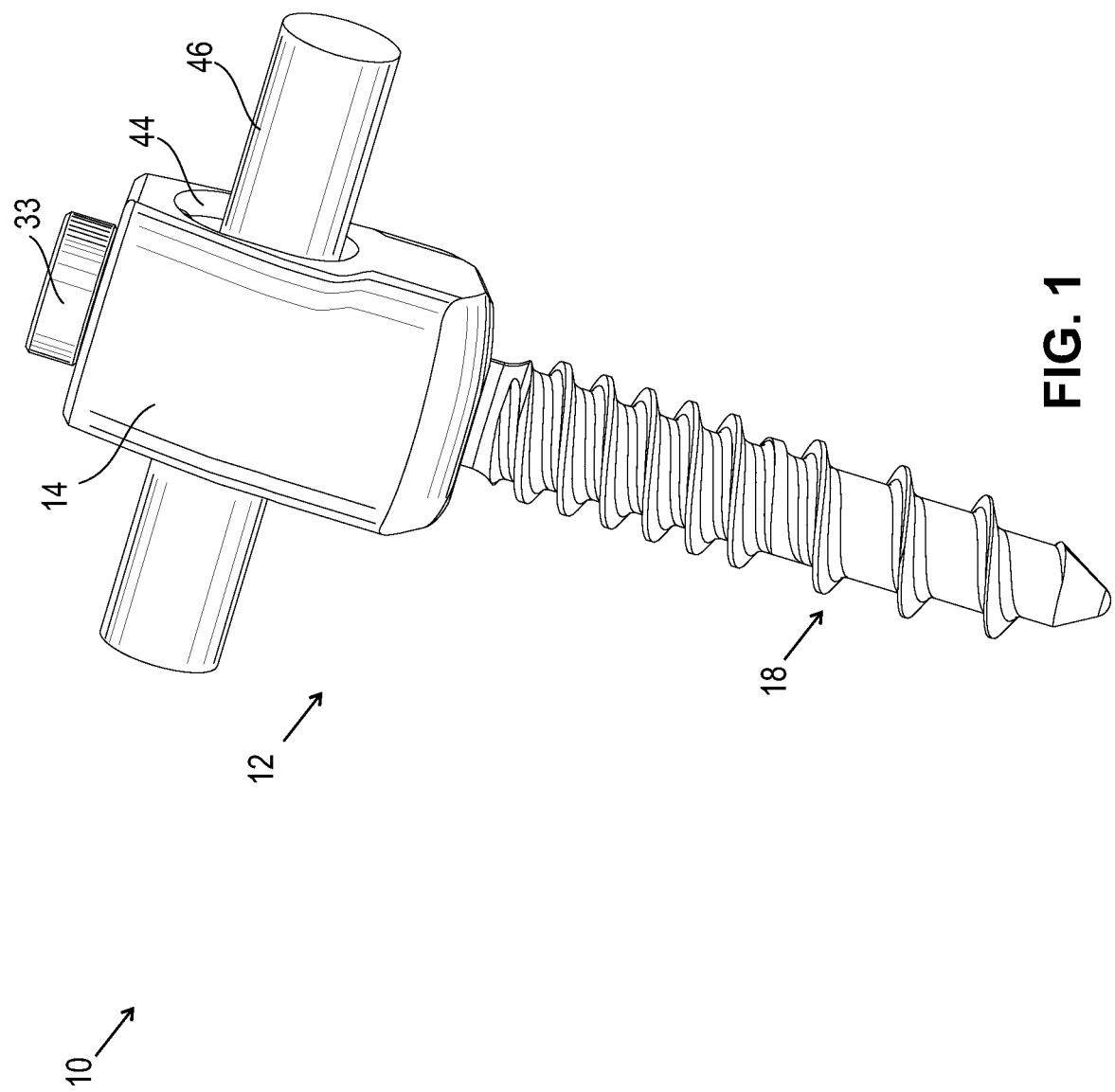
FIG. 1 is a perspective view of components of one embodiment of a spinal implant system in accordance with the principles of the present disclosure.

The exemplary embodiments of a surgical system and related methods of use disclosed are discussed in terms of medical devices for the treatment of musculoskeletal disorders and more particularly, in terms of a spinal implant system including a bone fastener. In some embodiments, the present system provides a spinal implant system comprising a modular bone fastener system including one or more biased angle spinal implants. In some embodiments, the present system provides a biased angle spinal implant having a closed receiver. In some embodiments, the present system provides a biased angle spinal implant having a top loading receiver. In some embodiments, the present disclosure provides a spinal implant system including posterior fixation components employed with spinal deformity procedures to treat a cervical, thoracic, lumbar and/or sacral region of a spine, and/or ilium.

In some embodiments, the present system includes a spinal construct, for example, a modular biased angle spinal implant. In some embodiments, the biased angle spinal implant includes a shaft configured for a modular connection with an implant receiver. In some embodiments, the present system provides a modular shaft that allows selection of alternately configured biased angle implant receivers, such as, for example, a top loading receiver and/or a closed receiver. In some embodiments, the various implant receivers are provided in a kit.

In some embodiments, the spinal implant system includes a modular spinal implant system including a bone fastener configured for posterior fixation. In some embodiments, the spinal implant system includes a bone fastener that is biased to facilitate a shaft rotational range of motion from −11 degrees to +41 degrees relative to a selected axis. In some embodiments, the system includes a closed bone fastener and a top load bone fastener. In some embodiments, the bone fastener includes an angled receiver configured for attachment to a threaded shaft. In some embodiments, the spinal implant system includes shaft assemblies and implant receiver/head assemblies that may be joined together during manufacturing or intra-operatively, for example, during a surgical procedure in an operating room. In some embodiments, the spinal implant system provides multiple surgical options while minimizing the amount of inventory stored in an operating room.

In some embodiments, the spinal implant system includes a biased bone fastener configured for iliac fixation. In some embodiments, the bone fastener is configured to accommodate a S2-alar-iliac (S2AI) fixation trajectory. In some embodiments, the bone fastener includes a receiver configured for 40 degrees of angulation relative to a selected axis, for example, a receiver axis. In some embodiments, the bone fastener is in a biased configuration, for example, a first portion of the receiver is angled relative to a second portion of the receiver and/or a shaft. In some embodiments, the bone fastener is in a biased configuration and engageable with a crown and a shaft to facilitate a rotational range of motion of the shaft for iliac fixation. In some embodiments, the portion of the receiver is biased 15 degrees and includes a range of motion of −11 degrees to +41 degrees. In some embodiments, the receiver includes a 15 degree angled cut on a distal end of the receiver.

In some embodiments, the spinal implant system includes a bone fastener including a closed multi-axial screw (CMAS). In some embodiments, the bone fastener is biased and includes a receiver including a channel configured for engagement with an instrument, including a universal head inserter/locker. In some embodiments, the channel is disposed along a longitudinal axis of the receiver. In some embodiments, the longitudinal axis is centrally disposed relative to the bone fastener. In some embodiments, the receiver includes an inner surface that defines one or more undercuts configured to engage with the universal head inserter/locker. In some embodiments, the bone fastener includes a crown configured for disposal with the receiver. In some embodiments, the crown includes a proximal opening. In some embodiments, the opening includes a vertical opening. In some embodiments, the opening is in alignment with the longitudinal axis. In some embodiments, the crown is configured for connection with a head of a shaft. In some embodiments, the head includes a tool engaging portion including a hexalobe configuration. In some embodiments, the diameter of the head is less than the diameter of the receiver. In some embodiments, a set screw is configured for engagement with the crown and is configured for disposal with the receiver. In some embodiments, the set screw is offset with the opening of the crown and is driven into alignment with the longitudinal axis by the universal head inserter/locker. In some embodiments, the shaft is pivotable relative to the receiver via engagement with an inner surface of the crown. In some embodiments, the inner surface of the crown is angled relative to the longitudinal axis.

In some embodiments, the crown is configured for disposal with the receiver. In some embodiments, the receiver includes an inner surface. In some embodiments, the inner surface includes one or more break away elements, including one or more welds. In some embodiments, the one or more welds are configured to retain the crown in an upright position within the receiver. In some embodiments, the inner surface of the receiver includes one or more spot welds, for example, four spot welds. In some embodiments, the spot welds are disposed about an interior circumference of the inner surface every 90 degrees. In some embodiments, the spot weld includes a frangible weld that is deformed to facilitate fracture and separation of the frangible weld when the bone fastener is locked with the universal head inserter/locker. In some embodiments, the one or more break away elements include an interference snap-fit connection between the inner surface and the crown. In some embodiments, the interference snap-fit connection includes a portion of the inner surface that snap engages around protrusions on a surface of the crown.

In some embodiments, the crown includes a keying feature to lock the crown with the receiver to prevent rotation of the crown within the receiver. In some embodiments, the keying feature includes a flat, hexalobe and/or a spline on the inner surface of the receiver and/or crown to fix the inner surface with the crown. In some embodiments, the keying feature incudes a thickened wall defined from the inner surface of the receiver that engages with the outer surface of the crown to prevent rotation of the crown within the receiver. In some embodiments, the shaft rotates greater than or less than 15 degrees relative to the receiver before a portion of the shaft contacts a distal end of the receiver. In some embodiments, the receiver attaches to the shaft vertically relative to the longitudinal axis of the receiver. In some embodiments, the receiver attaches to the shaft at an angle relative to the longitudinal axis.

In some embodiments, the present spinal implant system is employed with a method of assembly. In some embodiments, the method includes the step of inserting a crown within a receiver of a bone fastener. In some embodiments, the crown is inserted within the receiver from a proximal end of the receiver. In some embodiments, the method includes the step of inserting a resilient member, including an upper ring within an upper groove defined from the inner surface of the receiver. In some embodiments, the upper ring is compressed radially and hoop stress retains the upper ring within the upper groove. In some embodiments, the method includes the step of inserting a resilient member, including a lower ring within a lower groove defined from the inner surface. In some embodiments, the lower ring translates in a downward and upward direction between the lower groove and an expansion groove defined from the inner surface and can expand radially within the expansion groove. In some embodiments, the crown engages with the upper ring and drives the upper ring into the expansion groove. In some embodiments, the shaft is fixed with bone prior to connection with the receiver.

In some embodiments, the bone fastener is assembled with a force of less than 50 Newtons (N). In some embodiments, the bone fastener is selectively coupled with a non-instrumented assembly. In some embodiments, the non-instrumented assembly comprises manually engaging a shaft with a receiver of the bone fastener. In some embodiments, the non-instrumented assembly comprises manually engaging the shaft in a pop-on engagement with the receiver of the bone fastener. In some embodiments, a force required to manually engage the shaft with the receiver of the bone fastener in a non-instrumented assembly is in a range of 2 to 50 N. In some embodiments, a force required to manually engage the shaft with the receiver of the bone fastener in a non-instrumented assembly is in a range of 5 to 10 N. In some embodiments, the shaft is manually engaged with the receiver of the bone fastener in a non-instrumented assembly, as described herein, such that removal of the receiver from the shaft requires a force and/or a pull-out strength of at least 5000 N.

In some embodiments, the spinal system includes a bone fastener including top load multiaxial screw (MAS). In some embodiments, the bone fastener includes a receiver, a crown and a shaft. In some embodiments, the receiver and/or the crown includes a surface that defines a relief cut. In some embodiments, the relief cut is configured to maximize receiver geometry to resist splay when an implant is tightened with a setscrew. In some embodiments, the crown is welded to the inner surface of the receiver to create a frangible interface between the crown and the receiver.

In some embodiments, the present disclosure may be employed to treat spinal disorders, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a spinal implant system including a bone fastener, related components, methods of assembly and methods of employing the spinal implant system in accordance with the principles of the present disclosure. Alternate embodiments are also disclosed. Reference is made in detail to the exemplary embodiments of the present disclosure, which are illustrated in the accompanying figures. Turning to FIGS. 1-14, there are illustrated components of a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, for example, composites of metals and calcium-based ceramics, composites of PEEK and calcium based ceramics, composites of PEEK with resorbable polymers, totally resorbable materials, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a spinal construct, for example, a bone fastener 12, as shown in FIG. 1. Bone fastener 12 includes a biased configuration such that a member, for example, a receiver 14 includes a proximal portion that is angled relative to a distal portion to facilitate a range of motion of a shaft 18, as described herein. In some embodiments, receiver 14 is biased and engageable with a part, for example, a crown 16 and shaft 18 to facilitate a rotational range of motion of shaft 18 for iliac fixation. In some embodiments, bone fastener 12 is configured to accommodate a S2-alar-iliac (S2AI) fixation trajectory. In some embodiments, bone fastener 12 is configured for posterior fixation and for treating spinal deformities, including adult spinal deformities.

Figure 2:
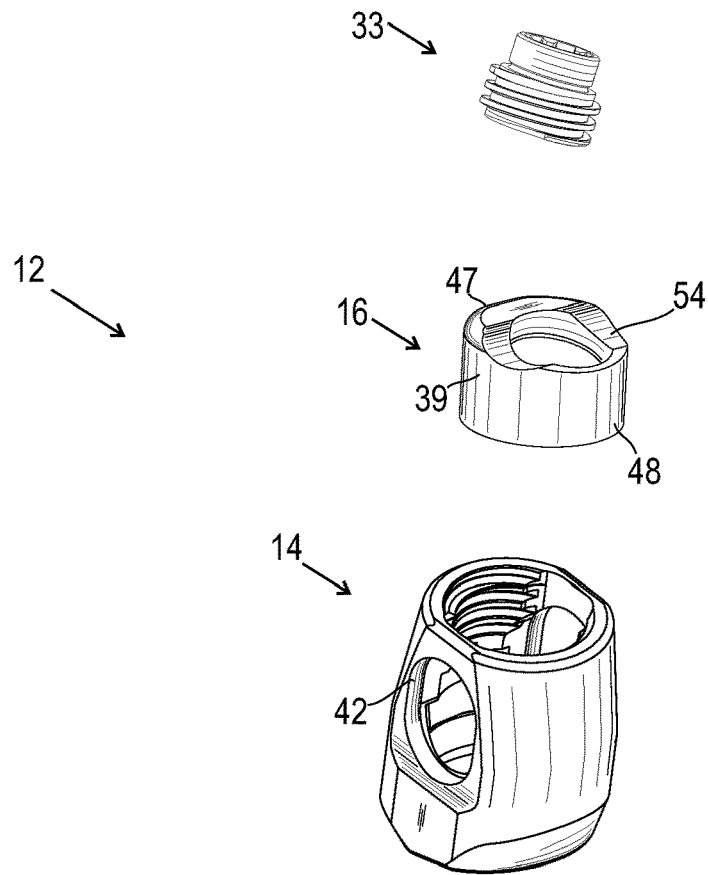
FIG. 2 is a perspective view of components of one embodiment of a spinal implant system in accordance with the principles of the present disclosure with parts separated.
Figure 2:
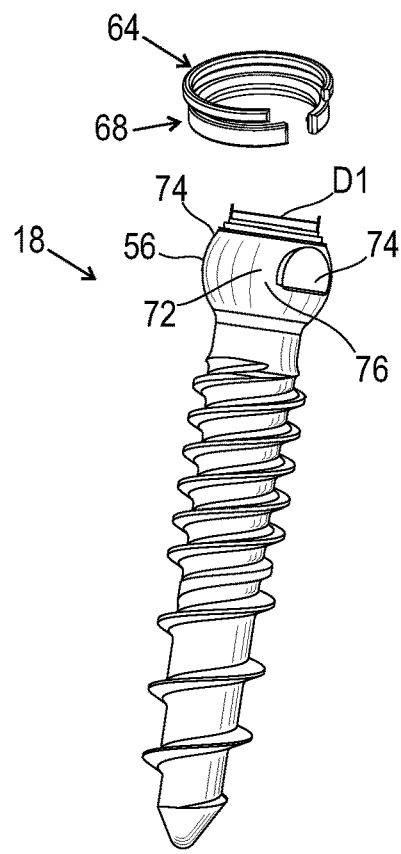
Figure 3:
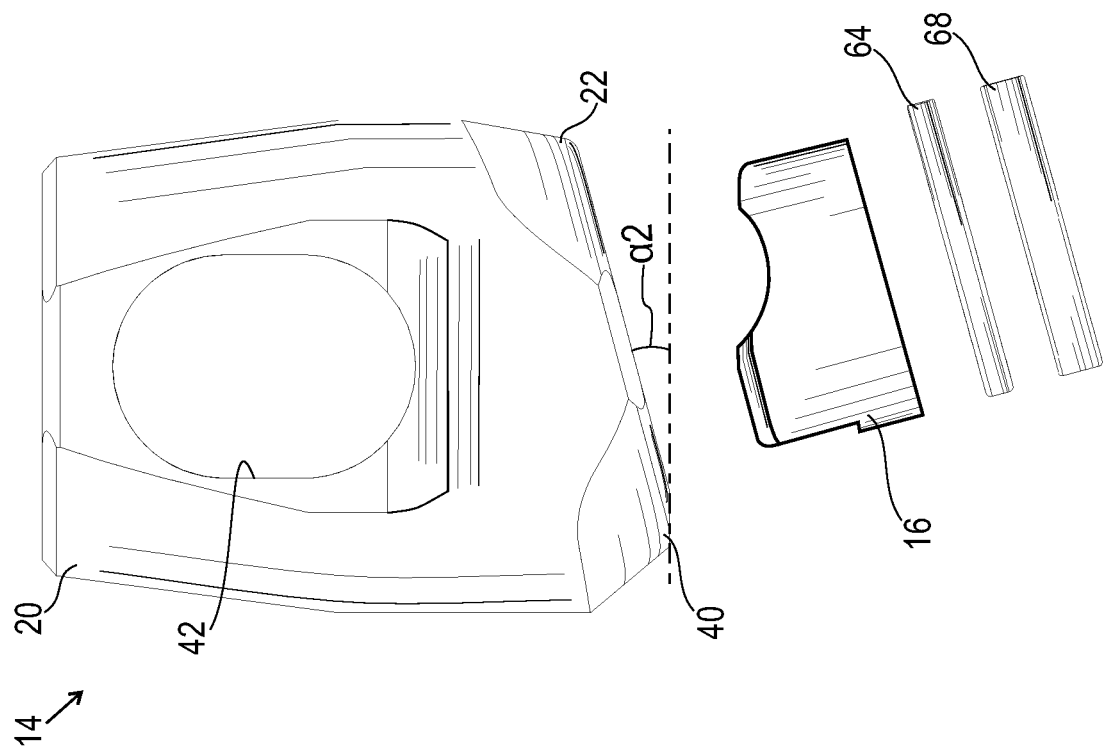
FIG. 3 is a perspective view of components of the system shown in FIG. 1 with parts separated.
Figure 6:
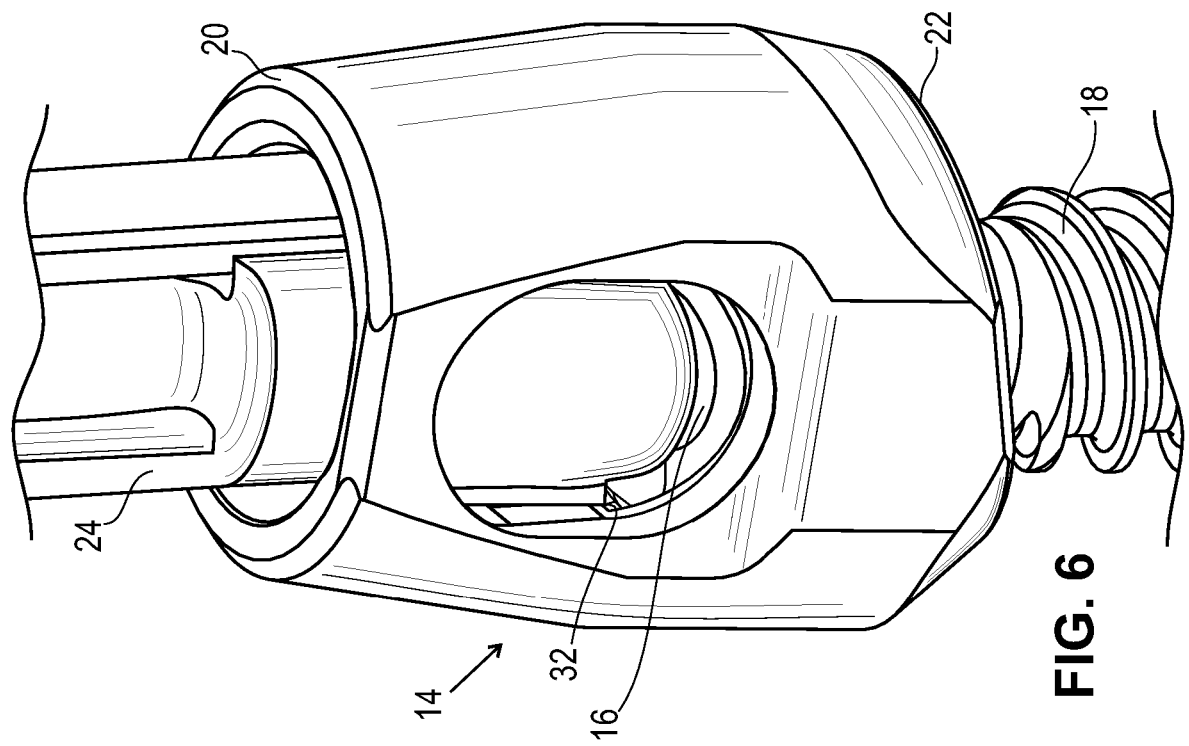
FIG. 6 is a break away perspective view of components of the system shown in FIG. 1 disposed with a surgical instrument.
Figure 5:
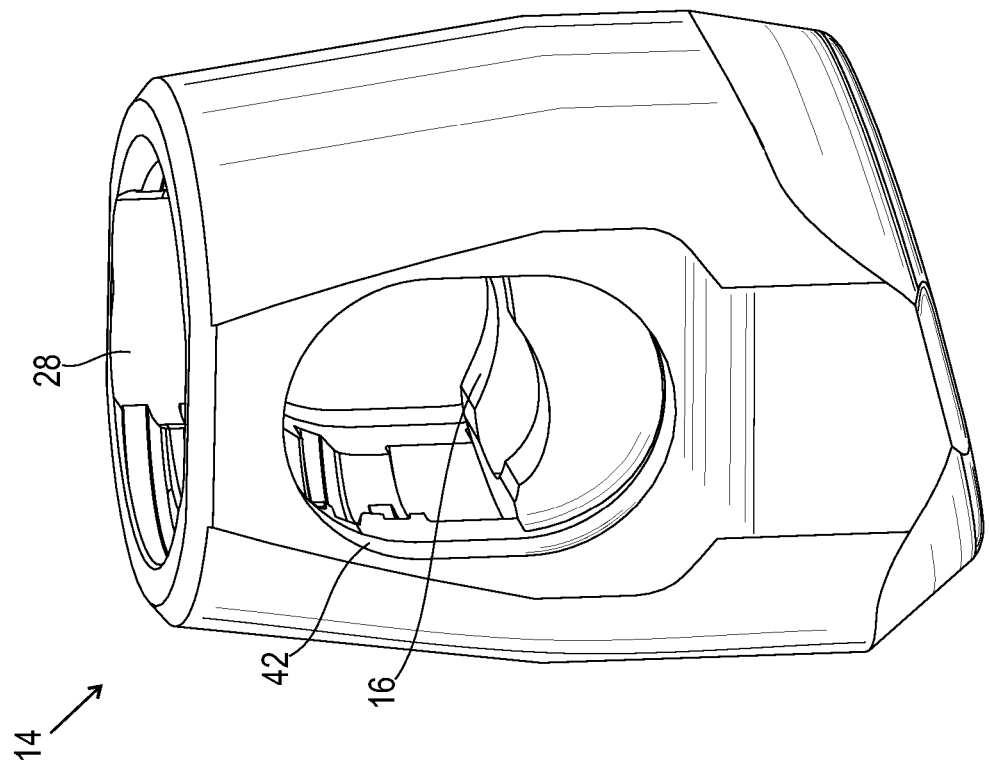
FIG. 5 is a perspective view of components of the system shown in FIG. 1.

Bone fastener 12 includes receiver 14 that is configured for engagement with crown 16 and shaft 18, as shown in FIG. 2. In some embodiments, receiver 14 is configured as a closed receiver that extends from a proximal portion 20 to a distal portion 22, as shown in FIG. 3. Portion 20 is configured for engagement with a surgical instrument, for example, an inserter 24, and portion 22 is configured for engagement with shaft 18, as shown in FIG. 6.

Figure 4:
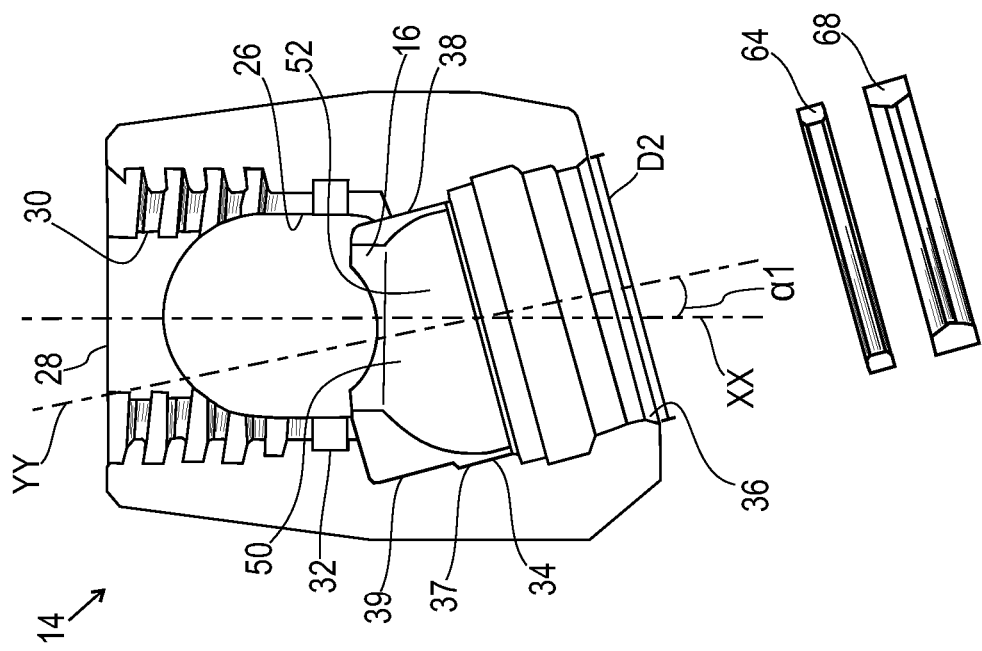
FIG. 4 is a cross section view of the components shown in FIG. 3.

Portion 20 defines a cavity 26, as shown in FIG. 4. Cavity 26 includes a proximal passageway 28 that defines a longitudinal axis XX. An interior wall 30 defines a groove 32 configured for engagement with inserter 24, as shown in FIGS. 4 and 6. Wall 30 is configured for engagement with a coupling member, for example, a set screw 33, as shown in FIGS. 1 and 2. In some embodiments, cavity 26 may have alternate cross section configurations, for example, oval, oblong, triangular, square, polygonal, irregular, uniform, non-uniform, offset, staggered, undulating, arcuate, variable and/or tapered. In some embodiments, cavity 26 may have alternate surface configurations, for example, rough, arcuate, undulating, mesh, porous, semi-porous, dimpled and/or textured. In some embodiments, cavity 26 may be disposed at alternate orientations, relative to axis XX, for example, transverse, perpendicular and/or other angular orientations such as acute or obtuse, coaxial and/or may be offset or staggered.

Portion 22 defines a cavity 34, as shown in FIG. 4. Cavity 34 is disposed at an angle relative to cavity 26 to facilitate a rotational range of motion of shaft 18 for iliac fixation. Cavity 34 includes a distal passageway 36 that defines a longitudinal axis YY, as shown in FIG. 4. Longitudinal axis YY is disposed relative to longitudinal axis XX at an angle $\alpha1$ in a range of about greater than 0 degrees to about 45 degrees. In some embodiments, longitudinal axis YY is disposed at an angle of 15 degrees relative to longitudinal axis XX. An inner surface 37 defines a wall 38 configured for engagement with an outer surface 39 of crown 16 for provisional fixation of crown 16 with portion 22, as shown in FIG. 4. In some embodiments, cavity 34 may have alternate cross section configurations, for example, oval, oblong, triangular, square, polygonal, irregular, uniform, non-uniform, offset, staggered, undulating, arcuate, variable and/or tapered. In some embodiments, cavity 34 may have alternate surface configurations, for example, rough, arcuate, undulating, mesh, porous, semi-porous, dimpled and/or textured. In some embodiments, cavity 34 may be disposed at alternate orientations, relative to axis YY and/or axis XX, for example, transverse, perpendicular and/or other angular orientations such as acute or obtuse, coaxial and/or may be offset or staggered.

Portion 22 includes an outer surface that defines an angled edge 40, as shown in FIG. 3. Edge 40 includes an angle $\alpha2$ configured to limit shaft 18 range of motion. In some embodiments, angle $\alpha2$ is in a range of more than 0 to about 30 degrees relative to longitudinal axis XX. In some embodiments, $\alpha2$ is 15 degrees. Edge 40, portion 22 and crown 16 facilitate a rotational range of motion of shaft 18 from −11 degrees to +41 degrees relative to longitudinal axis XX as a head 56 of shaft 18 engages crown 16 and edge 40 limits shaft 18 rotational range of motion. The outer surface defines openings 42, 44, as shown in FIGS. 1 and 2, configured for disposal of a longitudinal element, including a spinal rod 46, as shown in FIG. 1. Rod 46 is disposable in cavity 26 via openings 42, 44. In some embodiments, openings 42, 44 may have alternate cross section configurations, for example, oval, oblong, triangular, square, polygonal, irregular, uniform, non-uniform, offset, staggered, undulating, arcuate, variable and/or tapered.

Figure 10:
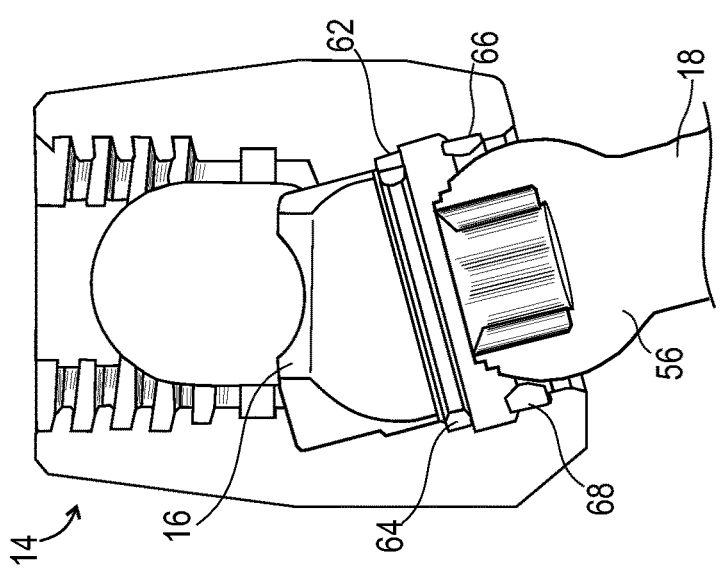
FIG. 10 is a cross section view of components of the system shown in FIG. 1.
Figure 14:
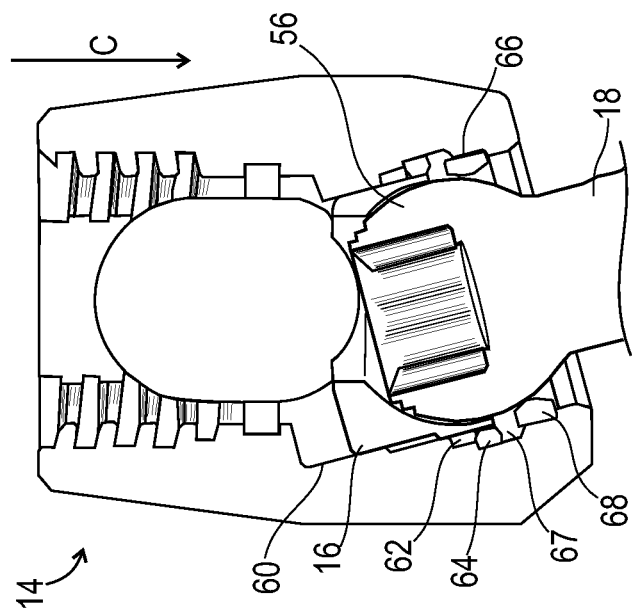
FIG. 14 is cross section view of components of the system shown in FIG. 1.

Outer surface 39 is configured to be releasably engageable with wall 38 of portion 22 such that crown 16 is movable between a provisional orientation, for example, a releasable engagement of crown 16 with receiver 14, as shown in FIG. 10, and a fixed orientation, for example, a fixed or permanent engagement of crown 16 with receiver 14 and shaft 18, as shown in FIG. 14 and described herein. Crown 16 extends between an end 47 and an end 48, as shown in FIG. 2. Outer surface 39 defines an opening 50 aligned with cavity 26 and longitudinal axis XX and an opening 52 aligned with cavity 34 and longitudinal axis YY, as shown in FIG. 4. Outer surface 39 defines a groove 54 at end 47, as shown in FIG. 2, configured for engagement with rod 46. In some embodiments, outer surface 39 may have alternate surface configurations, for example, rough, arcuate, undulating, mesh, porous, semi-porous, dimpled and/or textured. In some embodiments, groove 54 may have alternate surface configurations, for example, rough, arcuate, undulating, mesh, porous, semi-porous, dimpled and/or textured.

Figure 9:
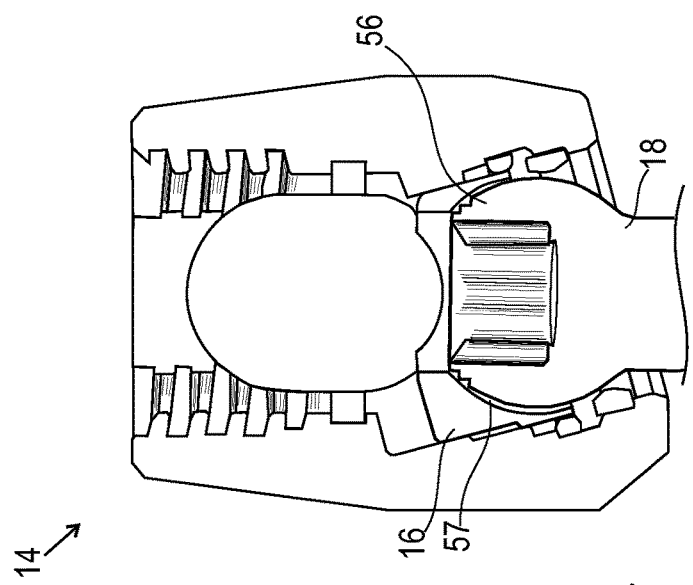
FIG. 9 is a cross section view of components of the system shown in FIG. 1.
Figure 8:
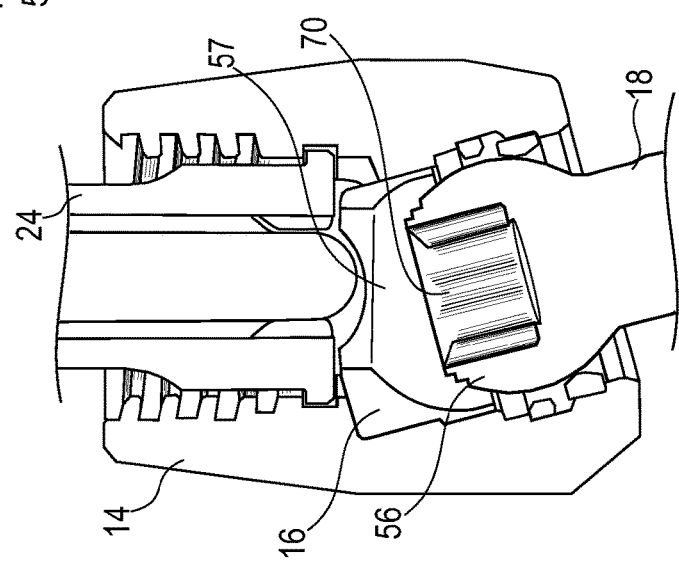
FIG. 8 is a cross section view of the components shown in FIG. 6.
Figure 7:
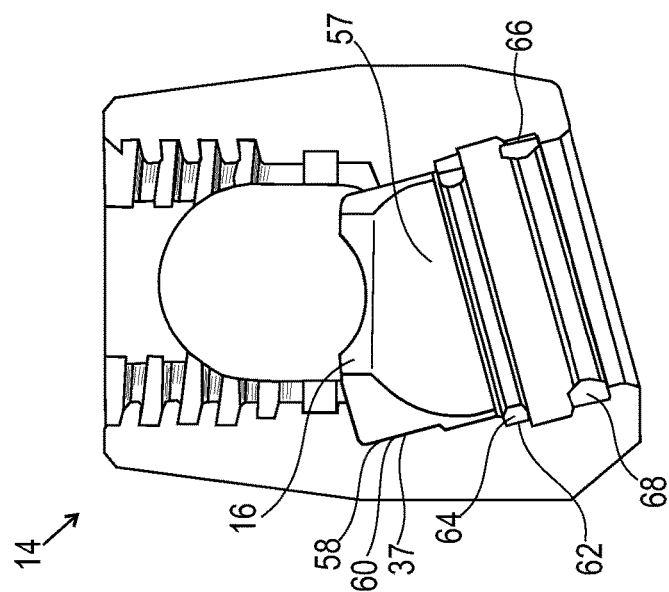
FIG. 7 is a cross section view of components of the system shown in FIG. 1.

Crown 16 includes an inner surface 57 configured for engagement with head 56 of shaft 18, as shown in FIGS. 7-9. In some embodiments, inner surface 57 may have alternate cross section configurations, for example, oval, oblong, triangular, square, polygonal, irregular, uniform, non-uniform, offset, staggered, undulating, arcuate, variable and/or tapered. In some embodiments, inner surface 57 may have alternate surface configurations, for example, rough, arcuate, undulating, mesh, porous, semi-porous, dimpled and/or textured.

Inner surface 37 includes a break away element 58, as shown in FIG. 7. Break away element 58 is configured to facilitate movement of crown 16 between the provisional orientation and the fixed orientation, as described herein. In the provisional orientation, break away element 58 is configured to connect crown 16 with distal portion 22 and to retain crown 16 in an upright position with portion 22. Break away element 58 releasably fixes crown 16 in the provisional orientation with receiver 14, as shown in FIG. 10 and described herein. Break away element 58 includes a frangible portion 60. In some embodiments, frangible portion 60 is circumferentially disposed about crown 16. In some embodiments, frangible portion 60 includes one or more deformable elements, for example, a tab, wire, projection, tang, rim, and/or bar to facilitate fracture and separation. In some embodiments, frangible portion 60 includes four frangible portions 60. In some embodiments, one or more frangible portions 60 are circumferentially disposed about wall 38 and/or crown 16 every 90 degrees. In some embodiments, frangible portion 60 is fabricated from a frangible material, including a rubber, adhesive, metal and/or a plastic. In some embodiments frangible portion 60 includes at least one weld, including at least one spot weld (not shown).

Frangible portion 60 is deformable to facilitate fracture and separation of frangible portion 60 when an instrument, for example, inserter 24 engages and applies force to crown 16 to connect crown 16 with head 56 of shaft 18, as shown in FIGS. 8 and 9. Frangible portion 60 deforms to position crown 16 in the fixed orientation with receiver 14 and shaft 18, as shown in FIG. 14. Frangible portion 60 has a pre-determined force limit. In some embodiments, the pre-determined force limit is in a range of 200 to 800 Newtons (N).

In some embodiments, break away element 58 includes an interference snap-fit connection between wall 38 and crown 16. In some embodiments, the interference snap-fit connection includes wall 38 that snap engages around protrusions (not shown) on outer surface 39 of crown 16.

In some embodiments, crown 16 includes a keying feature (not shown) to lock/fix crown 16 with wall 38 to prevent rotation of crown 16 within portion 22. In some embodiments, the keying feature includes a flat, flange, hexalobe and/or a spline on wall 38 and/or on crown 16. In some embodiments, the keying feature incudes a thickened wall 38 that engages with outer surface 39 of crown 16 to prevent rotation of crown 16 within portion 22.

Figure 11:
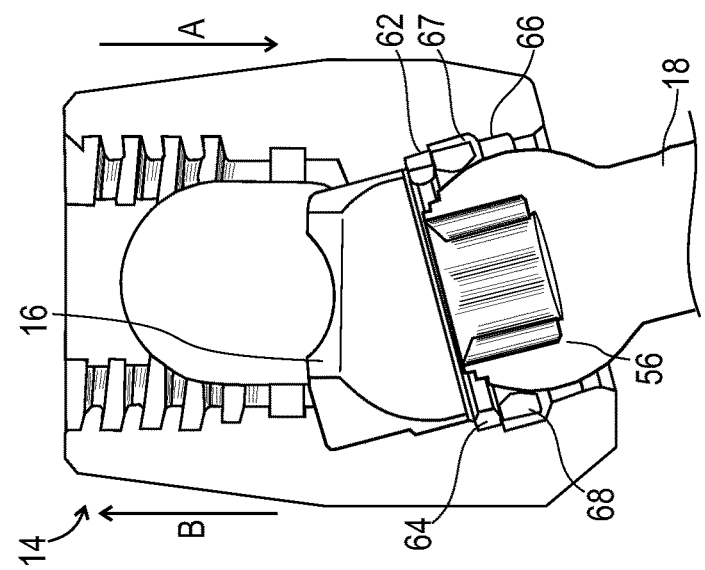
FIG. 11 is a cross section view of components of the system shown in FIG. 1.

Inner surface 37 of portion 22 defines a circumferential upper groove 62 configured for disposal of a resilient member, for example, a ring 64, as shown in FIGS. 2 and 14. Ring 64 is contractable in upper groove 62. Ring 64 includes a circumference that defines an opening, for example, a gap. In some embodiments, the gap is sized such that the gap has a thickness that is less than the height and the width. In some embodiments, the gap is sized to allow ring 64 to translate through portion 22 of receiver 14 by contracting circumferentially. In some embodiments, upon disposal of ring 64 with upper groove 62, surfaces of upper groove 62 resist and/or prevent axial translation of ring 64 relative to axis longitudinal axis XX. Inner surface 37 defines an expansion groove 67, as shown in FIG. 11.

Inner surface 37 defines a circumferential lower groove 66 configured for disposal of a resilient member, for example, a ring 68, as shown in FIGS. 2 and 14. Ring 68 is expandable in expansion groove 67. Ring 68 includes a circumference that defines an opening, for example, a gap. In some embodiments, the gap is sized such that the gap has a thickness that is less than the height and the width. In some embodiments, the gap is sized to allow ring 68 to translate through portion 22 of receiver 14 by contracting circumferentially. In some embodiments, upon disposal of ring 68 with lower groove 66, surfaces of lower groove 66 resist and/or prevent axial translation of ring 68 relative to axis longitudinal axis XX. Rings 64, 68 facilitate manual engagement/connection of receiver 14 and shaft 18. In some embodiments, rings 64, 68 facilitate manual engagement/connection of receiver 14 and shaft 18 such that shaft 18 is attached with receiver 14 in a non-instrumented snap-fit assembly, as described herein.

In some embodiments, manual engagement and/or non-instrumented assembly includes a practitioner, surgeon and/or medical staff grasping shaft 18 and receiver 14 and forcibly snap fitting the components together, as described herein. In some embodiments, manual engagement and/or non-instrumented assembly includes a practitioner, surgeon and/or medical staff grasping shaft 18 and receiver 14 and forcibly pop fitting the components together and/or pop fitting receiver 14 onto shaft 18, as described herein. In some embodiments, a force in a range of 2-50 N is required to manually engage shaft 18 and receiver 14 and forcibly assemble the components. For example, a force in a range of 2-50 N is required to snap fit and/or pop fit assemble shaft 18 and receiver 14. In some embodiments, a force in a range of 5-10 N is required to manually engage shaft 18 and receiver 14 and forcibly assemble the components. For example, a force in a range of 5-10 N is required to snap fit and/or pop fit assemble shaft 18 and receiver 14. In some embodiments, shaft 18 is manually engaged with receiver 14 in a non-instrumented assembly, as described herein, such that removal of receiver 14 and shaft 18 requires a force and/or a pull-out strength of at least 5000 N. In some embodiments, this configuration provides manually engageable components that are assembled without instrumentation, and subsequent to assembly, the assembled components have a selected pull-out strength and/or can be pulled apart, removed and/or separated with a minimum required force.

Shaft 18 is configured for fixation with tissue, for example, vertebral tissue. In some embodiments, shaft 18 rotates greater than or less than 15 degrees before a portion of shaft 18 contacts edge 40 of receiver 14, as described herein. In some embodiments, receiver 14 attaches to shaft 18 vertically relative to longitudinal axis XX. In some embodiments, receiver 14 attaches to shaft 18 at an angle relative to longitudinal axis XX to facilitate a rotational range of motion of shaft 18 for iliac fixation, as described herein.

In some embodiments, shaft 18 includes an outer surface having an external thread form. In some embodiments, the external thread form may include a single thread turn or a plurality of discrete threads. Head 56 of shaft 18 includes a tool engaging portion 70 configured to engage a surgical tool or instrument, as shown in FIG. 8 and described herein. In some embodiments, portion 70 includes a hexagonal cross-section to facilitate engagement with a surgical tool or instrument, as described herein. In some embodiments, portion 70 may have alternative cross-sections, for example, rectangular, polygonal, hexalobe, oval, or irregular.

Head 56 includes a diameter D1, as shown in FIG. 2. Diameter D1 of head 56 is less than a diameter D2 of portion 22 of receiver 14, as shown in FIG. 4, such that head 56 can engage with wall 38. Head 56 includes an outer surface 72, as shown in FIG. 2. In some embodiments, surface 72 includes planar surfaces, for example, flats 74 and arcuate surfaces 76 configured for engagement with crown 16, rings 64, 68, and/or wall 38 of portion 22, as shown in FIG. 14.

In some embodiments, spinal implant system 10 includes a spinal implant kit, as described herein, which includes a receiver 14 that is configured for selection from a plurality of alternate receivers and is configured for disposal with shaft 18 such that shaft 18 is interchangeable with the plurality of alternate receivers.

In assembly, operation and use, spinal implant system 10, similar to the systems and methods described herein, includes a receiver 14 for connection with a crown 16 and a shaft 18, and is employed with a surgical procedure for treatment of a spinal disorder affecting a section of a spine of a patient, as discussed herein. Spinal implant system 10 is employed with a surgical procedure for treatment of a condition or injury of an affected section of the spine.

In some embodiments, spinal implant system 10 comprises a spinal implant kit, which includes one or more selected interchangeable receivers, including receiver 14, configured for connection with one or more selected interchangeable crowns, including crown 16 and one or more selected interchangeable shafts, including shaft 18, to facilitate a rotational range of motion for iliac fixation, as described herein. In some embodiments, the one or more selected interchangeable shafts, including shaft 18, interface with one or more selected interchangeable receivers, including receiver 14 and one or more selected interchangeable crowns, including crown 16 to comprise one or more bone fastener 12 configurations. The components of bone fastener 12 and one or a plurality of spinal implants, for example, rod 46 can be delivered or implanted as a pre-assembled device or can be assembled in situ. The components of spinal implant system 10 may be completely or partially revised, removed or replaced.

In some embodiments, a shaft 18 is selected from the kit of the one or more interchangeable shafts for interchangeable connection with a selected receiver 14 from the one or more interchangeable receivers and a selected crown 16 from the one or more interchangeable crowns to comprise a bone fastener 12 having a selected movement including a shaft 18 rotational range of motion from −11 degrees to +41 degrees, as described herein.

Figure 12:
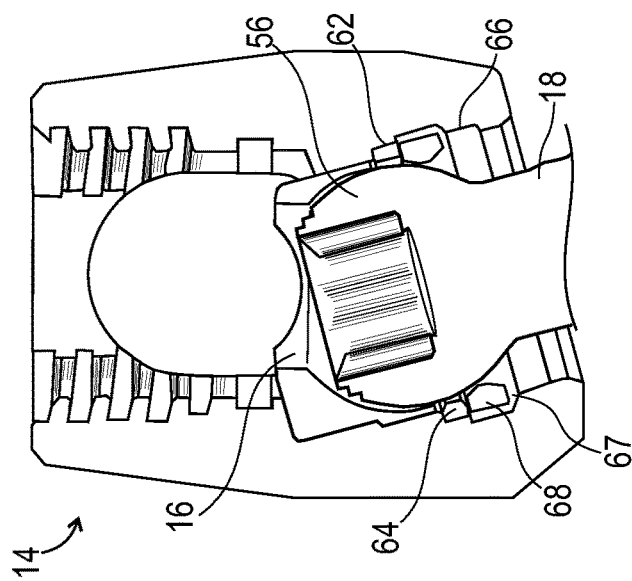
FIG. 12 is a cross section view of components of the system shown in FIG. 1.
Figure 13:
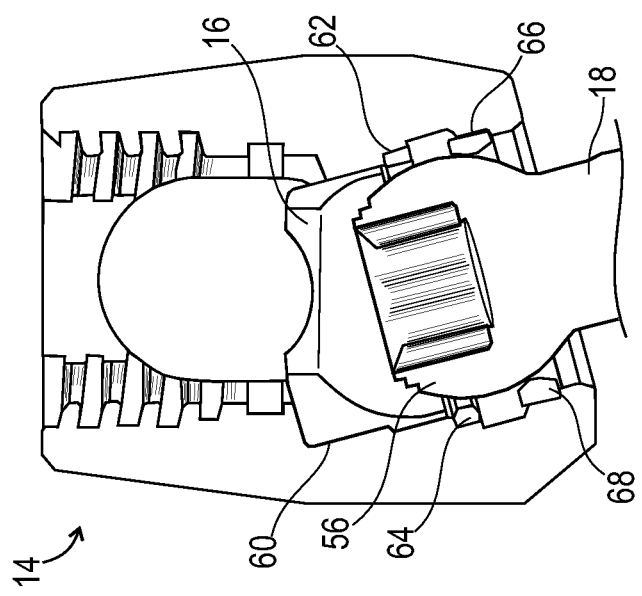
FIG. 13 is a cross section view of components of the system shown in FIG. 1.
Figure 15:
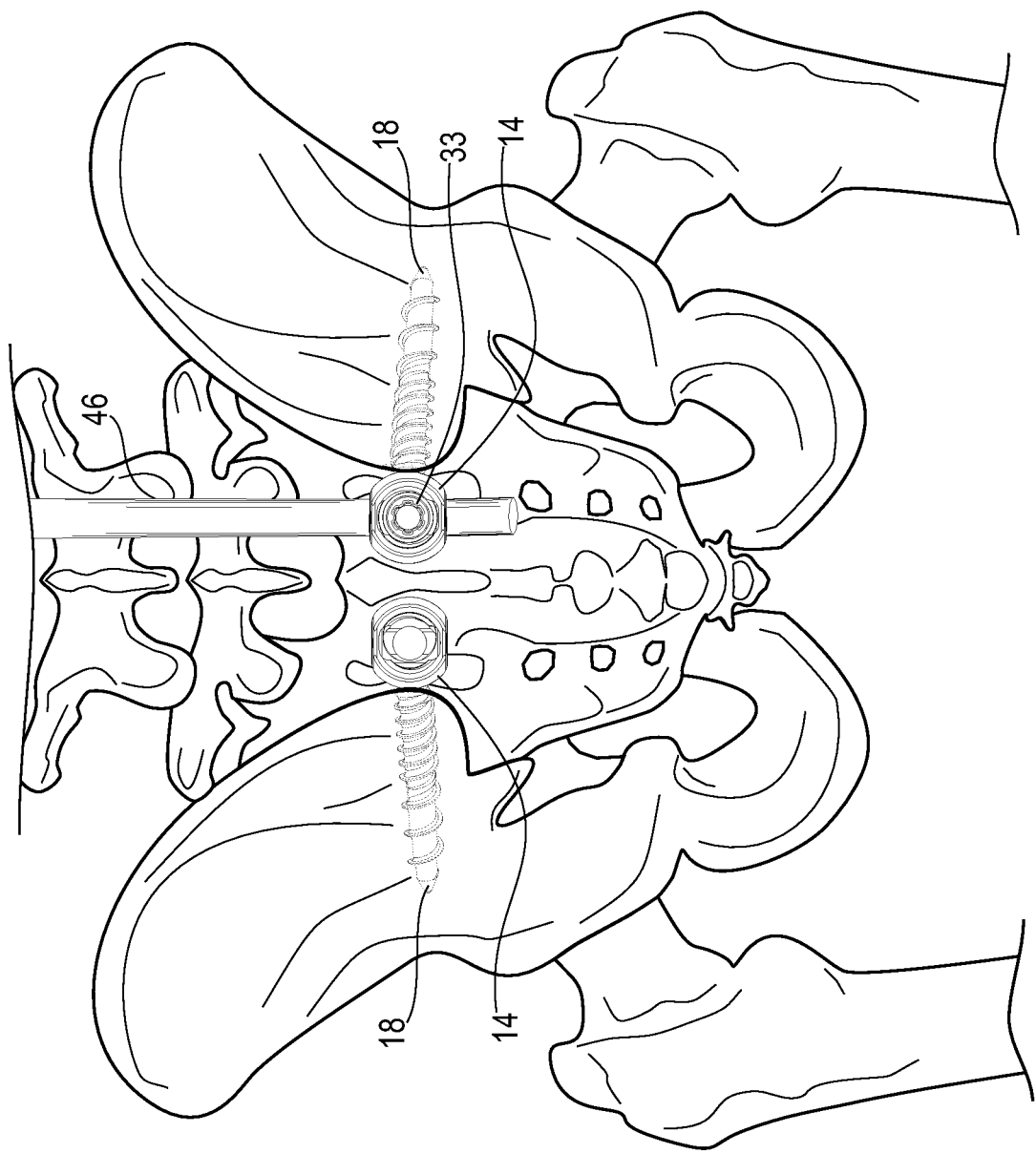
FIG. 15 is a plan view of components of one embodiment of a spinal implant system in accordance with the principles of the present disclosure disposed with patient anatomy.

In some embodiments, receiver 14 is assembled with crown 16, ring 64 and ring 68, as shown in FIG. 7. Ring 64 is disposed with upper groove 62 and ring 68 is disposed with lower groove 66 in a contracted orientation, as shown in FIG. 10. In some embodiments, bone fastener 12 is disposed adjacent vertebrae at a surgical site and is manipulated to drive, torque, insert or otherwise connect shaft 18 with vertebrae and/or the ilium in connection with a surgical procedure, as shown in FIG. 15 and described herein. Shaft 18 is engageable, as described herein, with receiver 14, as shown in FIG. 10. Receiver 14 is assembled with shaft 18 by translating receiver 14, in a direction shown by arrow A in FIG. 11. Engagement of head 56 with receiver 14 via passageway 36 causes a surface of head 56 to engage with ring 68 such that ring 68 is translated, in a direction shown by arrow B in FIG. 11, disposing ring 68 into expansion groove 67 in an expanded orientation. Head 56 translates further through receiver 14 in the direction shown by arrow B in FIG. 11 and passes further through ring 68 as ring 68 is driven back into lower groove 66, as shown in FIGS. 12 and 13. Ring 68 resiliently contracts into its natural state around head 56, as shown in FIG. 13.

Crown 16 is manipulated, for example, via engagement by inserter 24, as shown in FIG. 8, to translate crown 16, in a direction shown by arrow C in FIG. 14. Frangible portion 60 is deformed when inserter 24 engages and applies force to crown 16. Outer surface 39 of crown 16 engages ring 64 to dispose ring 64 into expansion groove 67 such that ring 64 resiliently opens into its natural orientation. Ring 64 is oriented for abutting and/or contacting engagement with ring 68 to resist and/or prevent translation of ring 68 from lower groove 66 into expansion groove 67, and thus providing fixed connection of the components of bone fastener 12 including permanent capture of head 56 and shaft 18, as shown in FIG. 14, in a configuration having a range of motion from −11 degrees to +41 degrees. Rod 46 is disposed within openings 42, 44, and engages end 47 via groove 54 of crown 16, as shown in FIGS. 1 and 2. Set screw 33 is disposed through passageway 28 and inserter 24 engages set screw 33 and applies torque to bring set screw 33 into alignment with longitudinal axis XX, and to engage set screw 33 with rod 46. Rod 46 is then brought into engagement with crown 16, as shown in FIG. 1.

In some embodiments, spinal implant system 10 includes an agent, which may be disposed, packed, coated or layered within, on or about the components and/or surfaces of spinal implant system 10. In some embodiments, the agent may include bone growth promoting material, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

In some embodiments, the use of microsurgical and image guided technologies may be employed to access, view and repair spinal deterioration or damage, with the aid of spinal implant system 10. The components of spinal implant system 10 can be made of radiolucent materials such as polymers. Radiomarkers may be included for identification under x-ray, fluoroscopy, CT or other imaging techniques.

In some embodiments, spinal implant system 10 can include one or a plurality of bone fasteners 12 such as those described herein and/or fixation elements, which may be employed with a single vertebral level or a plurality of vertebral levels. In some embodiments, bone fasteners 12 may be engaged with vertebrae in various orientations, for example, series, parallel, offset, staggered and/or alternate vertebral levels. In some embodiments, bone fasteners 12 may be configured as multi-axial screws, sagittal angulation screws, pedicle screws, mono-axial screws, uni-planar screws, fixed screws, anchors, tissue penetrating screws, conventional screws, expanding screws. In some embodiments, bone fasteners 12 may be employed with wedges, anchors, buttons, clips, snaps, friction fittings, compressive fittings, expanding rivets, staples, nails, adhesives, posts, connectors, fixation plates and/or post.

Figure 16:
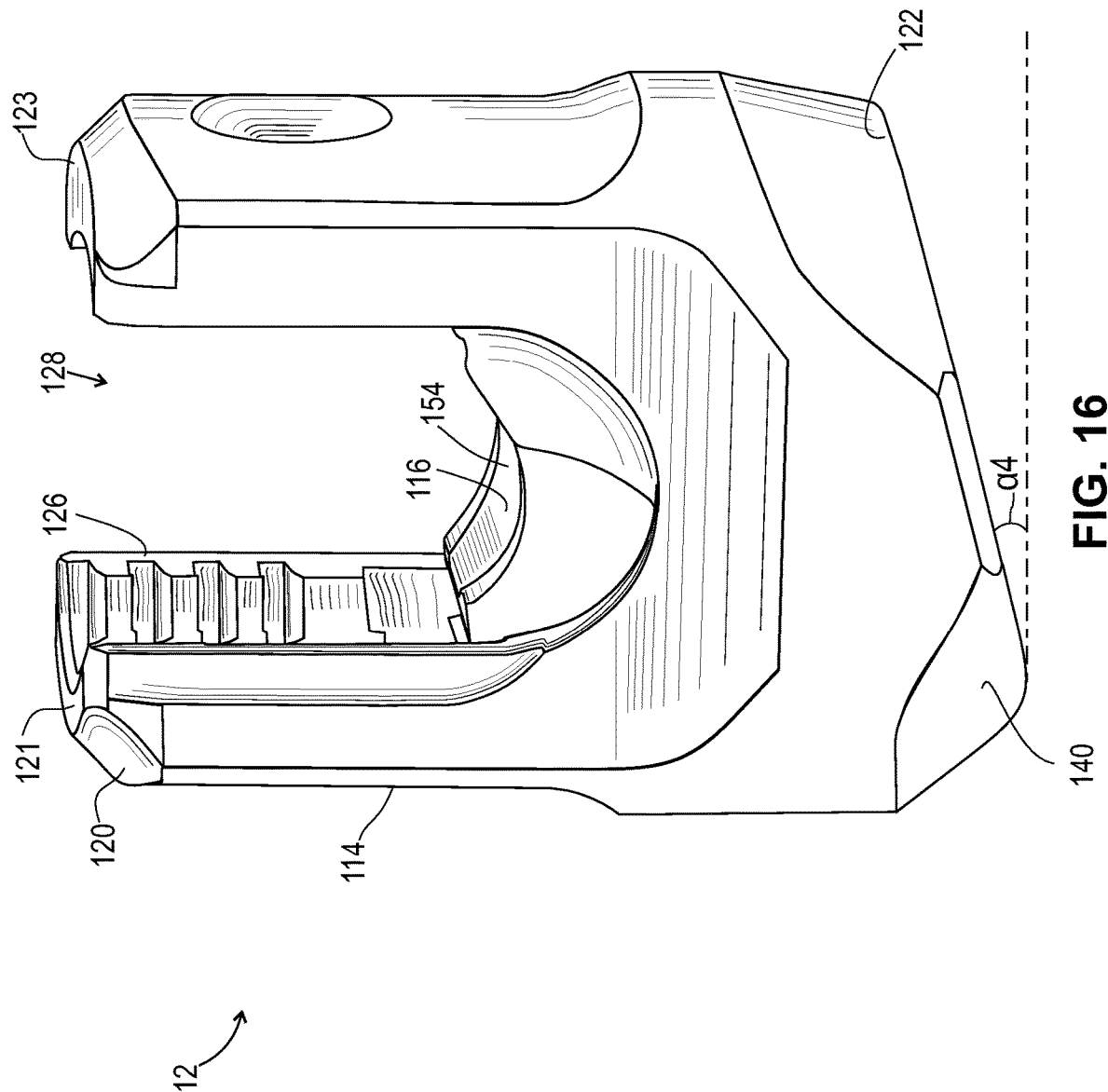
FIG. 16 is a perspective view of components of one embodiment of a spinal implant system in accordance with the principles of the present disclosure.
Figure 17:
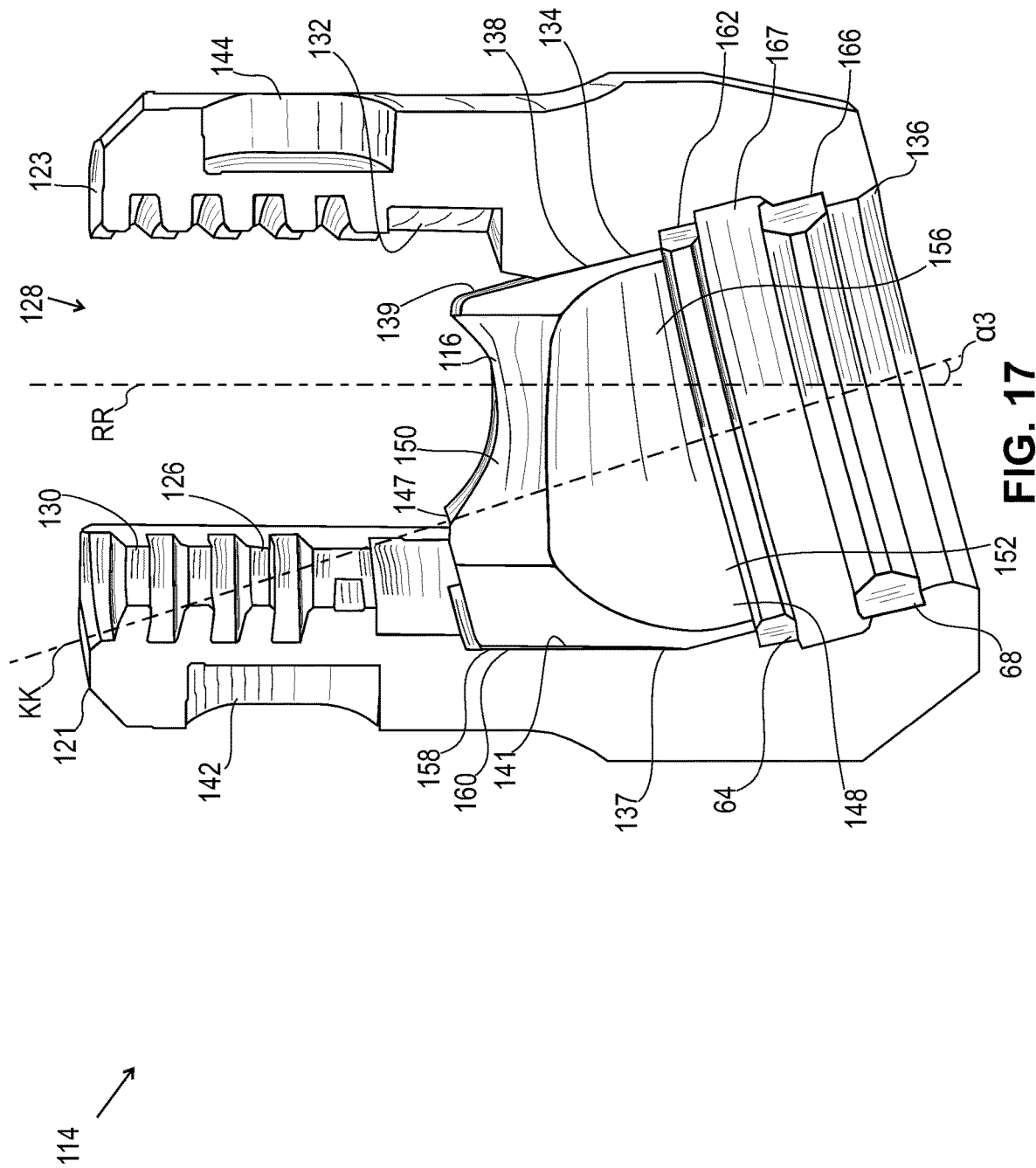
FIG. 17 is a cross section view of components of the system shown in FIG. 17.

In one embodiment, as shown in FIGS. 16 and 17, spinal implant system 10, similar to the systems and methods described above with regard to FIGS. 1-15, includes biased bone fastener 12 having a receiver 114. Receiver 114 includes a distal portion that is angled relative to a proximal portion to facilitate a rotational range of motion of shaft 18, similar to that described herein. Receiver 114 includes a biased top load receiver that extends from a proximal portion 120 to a distal portion 122, as shown in FIG. 16. Portion 120 is configured for engagement with inserter 24, and portion 122 is configured for engagement with shaft 18.

Portion 120 includes a pair of spaced apart arms 121, 123, as shown in FIG. 16. Portion 120 defines a cavity 126, similar to cavity 26 described herein. Cavity 126 includes a proximal passageway 128 that defines a longitudinal axis RR, as shown in FIG. 17. An interior wall 130 defines a groove 132 configured for engagement with inserter 24.

Portion 122 defines a cavity 134, as shown in FIG. 17, similar to cavity 34 described herein. Cavity 134 is disposed at an angle relative to cavity 126 to facilitate a rotational range of motion of shaft 18 for iliac fixation. Cavity 134 includes a distal passageway 136 that defines a longitudinal axis KK. Longitudinal axis KK is disposed relative to longitudinal axis RR at an angle α3 in a range of about greater than 0 degrees to about 45 degrees. In some embodiments, longitudinal axis KK is disposed at an angle of 15 degrees relative to longitudinal axis RR. An inner surface 137 defines a wall 138 configured for engagement with an outer surface 139 of crown 116, for provisional fixation of crown 116 with portion 122.

Portion 122 includes an outer surface that defines an angled edge 140, as shown in FIG. 16, similar to edge 40. Edge 140 includes an angle α4 configured to limit shaft 18 range of motion. In some embodiments, angle α4 is in a range of more than 0 to about 30 degrees. In some embodiments, α4 is 15 degrees. Edge 140, portion 122 and crown 116 facilitate a rotational range of motion of shaft 18 from −11 degrees to +41 degrees relative to longitudinal axis RR, as head 56 of shaft 18 engages crown 116 and edge 140 limits shaft 18 rotational range of motion. The outer surface defines openings 142, 144 configured for disposal of a longitudinal element, including rod 46.

Outer surface 139 of crown 116 is configured to be releasably engageable with wall 138 of portion 122 such that crown 116 is movable between a provisional orientation with receiver 114 and a fixed orientation with receiver 114 and shaft 18, similar to that described herein. Crown 116 extends between an end 147 and an end 148, as shown in FIG. 17. Outer surface 139 defines an opening 150 aligned with cavity 126 and longitudinal axis RR and an opening 152 aligned with cavity 134 and longitudinal axis KK, as shown in FIG. 17. Outer surface 139 defines a groove 154 at end 147, as shown in FIG. 16, configured for engagement with rod 46.

Outer surface 139 defines a relief 141 configured to facilitate expansion of crown 116 within portion 122. In some embodiments, relief 141 includes a cut, groove, recess, and/or flange. In some embodiments, outer surface 139 defines one or more reliefs disposed about a circumference of crown 116. Crown 116 includes an inner surface 157, similar to inner surface 57, configured for engagement with head 56 of shaft 18.

Inner surface 137 of portion 122 includes a break away element 158, similar to break away element 58, as shown in FIG. 17. Break away element 158 is configured to facilitate movement of crown 116 between the provisional orientation and the fixed orientation, similar to that described herein. In the provisional orientation, break away element 158 is configured to connect crown 116 with distal portion 122 and to retain crown 116 in an upright position with portion 122. Break away element 158 releasably fixes crown 116 in the provisional orientation with receiver 114, similar to that described herein. Break away element 158 includes a frangible portion 160, which is deformable to facilitate fracture and separation of frangible portion 160 when inserter 24 engages and applies torque to crown 116 to connect crown 116 with head 56 of shaft 18. Frangible portion 160 deforms to position crown 116 in the fixed orientation with receiver 114 and shaft 18.

Inner surface 137 of portion 122 defines a circumferential upper groove 162 configured for disposal of ring 64. Ring 64 is contractable in upper groove 162. Inner surface 137 defines an expansion groove 167. Inner surface 137 defines a circumferential lower groove 166 configured for disposal of ring 68. Ring 68 is expandable in lower groove 166. Rings 64, 68, upper groove 162, expansion groove 167 and lower groove 166 are configured to facilitate provisional capture of shaft 18, similar to that described herein. In some embodiments, rings 64, 68 facilitate manual engagement/connection of receiver 114 and shaft 18 such that shaft 18 is attached with receiver 114 in a non-instrumented snap-fit assembly, similar to that described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct comprising:
    a first member including a proximal portion defining a first cavity, and a distal portion defining a second cavity disposed at an angle relative to the first cavity,
    the distal portion being configured for connecting with a second member, the second member being configured for fixation with vertebral tissue;
    a crown defining a first opening aligned with the first cavity and a second opening aligned with the second cavity; and
    a break away element connecting the crown and the distal portion.

2. The spinal construct as recited in claim 1, wherein the first cavity includes a proximal passageway defining a first longitudinal axis and the second cavity includes a distal passageway defining a second longitudinal axis, the second axis being disposed relative to the first axis at an angle in a range of about greater than 0 degrees to about 45 degrees.

3. The spinal construct as recited in claim 2, wherein the second axis is disposed at an angle of 15 degrees relative to the first axis.

4. The spinal construct as recited in claim 1, wherein the crown includes an outer surface being provisionally fixable with an inner surface of the distal portion.

5. The spinal construct as recited in claim 1, wherein the crown includes an outer surface being releasably engageable with an inner surface of the distal portion.

6. The spinal construct as recited in claim 5, wherein the crown is releasably engageable with the inner surface such that the crown is movable between a provisional orientation with the first member and a fixed orientation with the second member.

7. The spinal construct as recited in claim 1, wherein the break away element includes a frangible portion having a pre-determined force limit.

8. The spinal construct as recited in claim 1, wherein the break away element includes at least one weld circumferentially disposed about the crown.

9. The spinal construct as recited in claim 1, wherein the crown includes an outer surface defining a relief configured to allow expansion of the crown.

10. The spinal construct as recited in claim 1, wherein the first member is manually engageable with the second member to connect the members in a non-instrumented snap-fit assembly.

11. The spinal construct as recited in claim 1, wherein the distal portion includes a first groove configured for disposal of a first resilient member that is contractable in the first groove, and a second groove configured for disposal of a second resilient member that is expandable in the second groove to connect the members.

12. The spinal construct system as recited in claim 1, wherein the first member includes a receiver that is selected from a plurality of alternate receivers and is configured for disposal with the second member such that the second member is interchangeable with the plurality of alternate receivers.

13. The spinal construct as recited in claim 1, wherein the first member includes a closed receiver.

14. A bone fastener comprising:
- a receiver including a proximal portion defining a first cavity, and a distal portion defining a second cavity disposed at an angle relative to the first cavity;
- a shaft connected with the distal portion and configured for fixation with vertebral tissue;
- a crown defining a first opening aligned with the first cavity and a second opening aligned with the second cavity; and
- a break away element connecting the crown and the distal portion,
- the crown being releasably engageable with an inner surface of the distal portion such that the crown is movable between a provisional orientation with the receiver and a fixed orientation with the receiver and the shaft.

15. The bone fastener as recited in claim 14, wherein the first cavity includes a proximal passageway defining a first longitudinal axis and the second cavity includes a distal passageway defining a second longitudinal axis, the second axis being disposed relative to the first axis at an angle in a range of about greater than 0 degrees to about 45 degrees.

16. The bone fastener as recited in claim 14, wherein the receiver and the shaft are manually engageable for connection in a non-instrumented snap-fit assembly.

17. A spinal implant system comprising:
- a first member including a proximal portion defining a first cavity, and a distal portion defining a second cavity disposed at an angle relative to the first cavity;
- a second member connectable with the distal portion and being configured for fixation with vertebral tissue;
- a crown defining a first opening aligned with the first cavity and a second opening aligned with the second cavity;
- a break away element connecting the crown and the distal portion; and
- a longitudinal element disposable in the first cavity.

18. The spinal implant system as recited in claim 17, wherein the first member includes a receiver that is selected from a plurality of alternate receivers and is configured for disposal with the second member such that the second member is interchangeable with the plurality of alternate receivers.

* * * * *